United States Patent [19]

Jacob

[11] Patent Number: 4,486,191
[45] Date of Patent: Dec. 4, 1984

[54] TAMPON

[75] Inventor: Joseph Jacob, Wooster, Ohio

[73] Assignee: Technology Unlimited Inc., Wooster, Ohio

[21] Appl. No.: 407,468

[22] Filed: Aug. 12, 1982

[51] Int. Cl.³ .............................................. A61F 5/46
[52] U.S. Cl. .................................................. 604/330
[58] Field of Search ........................ 604/330, 317, 328

[56] References Cited

U.S. PATENT DOCUMENTS

| | | | |
|---|---|---|---|
| 2,845,071 | 7/1958 | Wade | 604/330 X |
| 2,943,625 | 7/1960 | Lotts | 604/330 |
| 3,102,541 | 9/1963 | Adams | 604/330 X |
| 3,157,180 | 11/1964 | Bakunin | 604/330 |
| 3,841,333 | 10/1974 | Zalucki | 604/330 |
| 4,018,225 | 4/1977 | Elmi | 604/330 |

Primary Examiner—John D. Yasko
Attorney, Agent, or Firm—Ray S. Pyle; Robert Frijouf

[57] ABSTRACT

A catamenial device which is a tampon having a hollow or loosely packed central area and a forward end which flares open to a funnel configuration upon insertion into the vaginal tract of the user to cap the cervix and thereby direct menstrual fluid into the interior thereof. The tampon is removed by pulling a drawstring which is also a pursing string. The string first closes the forward end before exerting removal force on the tampon. Also, the body of the tampon is encased in a fluid barrier so that fluid is captured and retained within the tampon and absorption by the tampon from the vaginal wall is prevented.

8 Claims, 7 Drawing Figures

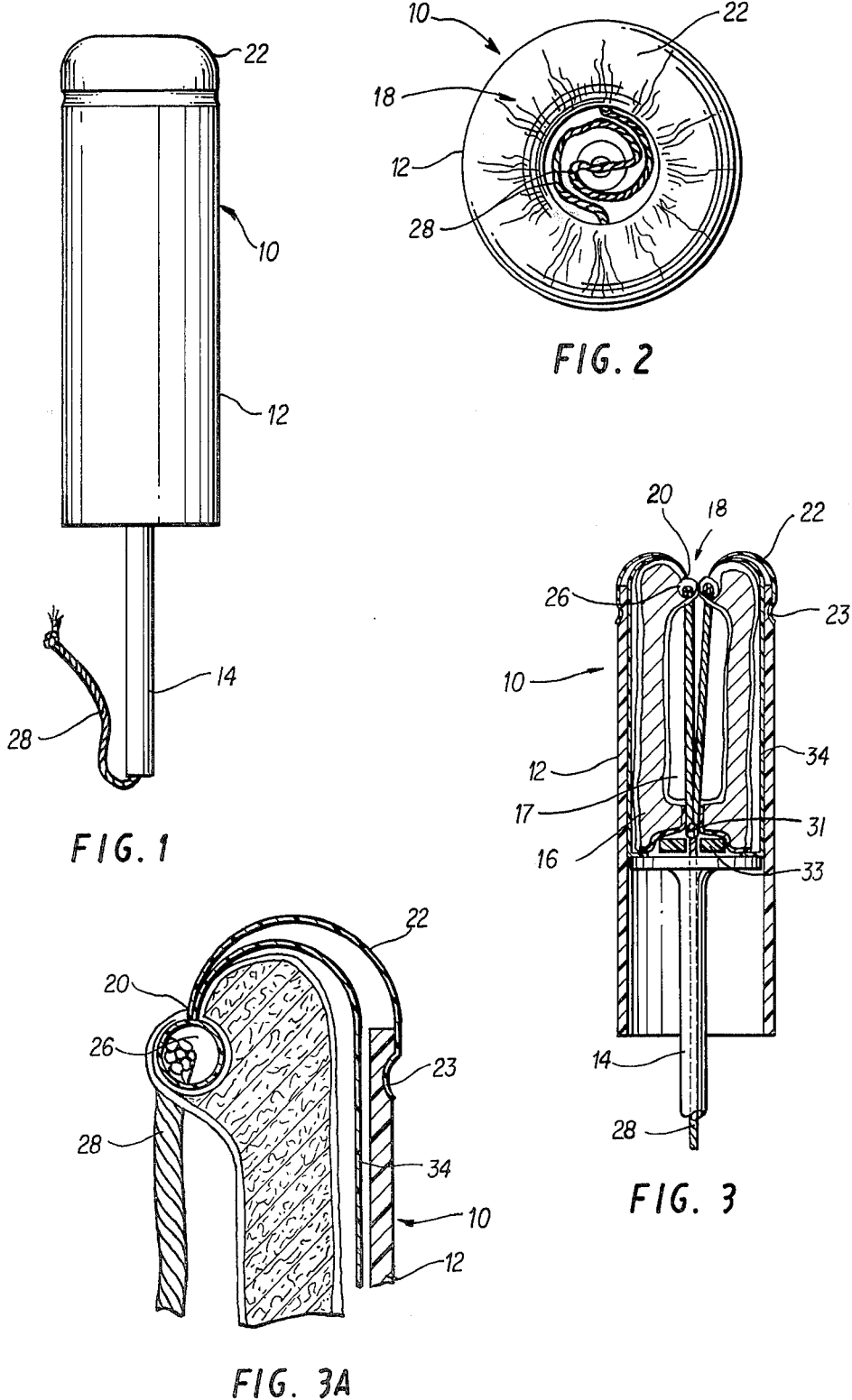

TAMPON

BACKGROUND OF THE INVENTION

A tampon is defined by *Webster's New 20th Century Dictionary* as a plug of cotton or other absorbent material placed into a wound, cavity, etc. for the control of hemorrhage or the absorption of secretions. The word has become almost exclusively the name of a form of the product used by women during menstruation.

The effort by the industry supplying tampons has been to create more and more absorbency in order to necessitate fewer changes by the user. There has been very little departure from the original cylindrical cotton body except in the mechanical art of insertion and in the absorbency of the body itself.

SUMMARY OF THE INVENTION

This product satisfies the requirements of a completely effective tampon including complete absorption of menstrual fluid. These criteria are met in such a way that the anatomical and physiological environment of the vaginal tract are not adversely disturbed. For example, the interfaces between the tampon and the mucosa are designed to be compatible and non-ulcerating. The common problem of channeling of the menstrual fluid around the tampon is avoided by design and not by pressure packing. Partial emptying of the tampon of its potentially toxic contents is prevented by a unique pursing closure system which is activated upon tampon removal. Only recently has new information been obtained on the role of catamenial products in the pathogenisis of potentially serious diseases such as Toxic Shock Syndrome, and therefore, it is an object of this invention to produce a product that will offer both high performance and safety.

The tampon is a substantially tubular body of absorbent material which, upon being inserted into the vagina will flower to an open funnel position and cap the cervix whereby essentially all of the menstrual fluid is captured and directed into an inward channel of the tampon.

It is also an object of the invention to produce a container effect of the tampon by preventing moisture absorbency through the lower portion of the tampon from an area which produces no menstrual blood. A conventional tampon will extract moisture from the vagina and cause excess drying and possible adverse results to the vaginal tissue.

This product satisfies the requirements of a completely effective tampon, including complete absorption of menstrual fluid. These criteria are met in such a way that the anatomical and physiological environment of the vaginal tract are not adversely disturbed.

Set forth below is a set of Anatomical an Physiological Considerations and Problems in separately numbered paragraphs. The means of satisfying the conditions and meeting the problems according to this invention are set forth as lettered paragraphs following each numbered paragraph.

1. All menstrual fluids flow from the uterus down into the vagina through an opening in the cervix (cerival os).

A. The tampon, upon insertion into the vagina, will flower open to an open funnel position and cap the cervix capturing the menstrual fluid which is directed into an inner chamber of the tampon.

2. The fluid products of menstruation are intended to pass rapidly through the vagina and be excreted. Freshly released menstrual fluid is only mildly toxic, but stagnant fluid both decomposes rapidly to form toxic substances and also supports microbial growth which produces toxins, which are causative factors for diseases such as the Toxic Shock Syndrome.

B. The menstrual fluid is trapped within the highly absorbent inner chamber of the tampon and is no longer able to have contact with the vaginal tissue, i.e. the fluid is essentially removed from the body upon being released by the cervix.

3. The vaginal glands release their own fluids which coat the vaginal tissues and are intended to protect the vaginal tissues from the menstrual fluids. Currently marketed high absorbency tampons remove this protective layer of vaginal fluids along with the menstrual fluids. This indiscriminate removal and subsequent drying and ulceration has been implicated strongly by medical scientists at the Center for Disease Control (CDC) as an important mechanism in the development of the Toxic Shock Syndrome.

C. This tampon is designed to absorb only the menstrual fluids as they are released from the cervix by means of a highly absorbent funnel system around the cervical os. The protective vaginal secretions are not absorbed by this tampon. This selective absorbency is achieved by having a non-absorbent outer covering over the lower exterior of the tampon which corresponds to the anatomical area which has the protective secretions. The non-absorbent outer layer of the tampon and the secretion covered vaginal tissue provide a compatible, non-ulcerating interface which protects the body from any noxious substance.

4. Channeling of menstrual fluids around tampons has been a problem. It occurs because the vagina (birth canal) has many folds which provide channels (thus the term channeling) for the menstrual fluid to flow around the ordinary tampon, thus resulting in tampon failure.

D. This tampon avoids channeling by its funneling design. All of the menstrual fluid is trapped by the absorbent funnel and directed into the inner retaining chamber. This is in contrast to currently marketed products which solve the problem by having the tampon expand upon wetting, producing a pressure pack to prevent the channeling.

5. The anatomical configuration of the vaginal tract is such that the inner cavity is larger than the narrowed exterior opening. The consequence of this is that currently marketed tampons, which are designed to expand in an unrestricted fashion in order to eliminate channeling, must be squeezed during removal. The squeezing action causes "stagnant menstrual fluid" (see number 2) to be released into the inner vaginal cavity and possibly retained where toxic substances can be absorbed through ulcerated areas of the vaginal wall, possibly producing serious illnesses or death.

E. This tampon is a complete collector of menstrual fluid without requiring expansion. It is in fact restricted in its expansion by its tubular, nonabsorbent exterior surface. Therefore, upon removal it is not squeezed like other tampons. An additional safety feature of this tampon is its unique pursing closure system which is activated upon the tampon's removal. The closure system prevents stagnant menstrual fluid from escaping during removal.

DETAILED DESCRIPTIONS OF THE DRAWINGS

FIG. 1 is an exterior view of a commercial embodiment of the tampon as supplied to the user.

FIG. 2 is a top end view of the tampon with the drawstring illustrated diagramatically in that it is unencased in the hemmed edge of the forward peripheral edge.

FIG. 3 is a vertical section in smaller size than the FIG. 2, illustrating the pursed condition of the forward end either before use or after extraction.

FIG. 3A is an enlarged detail of one section of the forward end of FIG. 3 illustrating the hemmed encasement of the drawstring for pursing and the membrane encasement for opening restriction.

DETAILED DESCRIPTION

Figure 4:
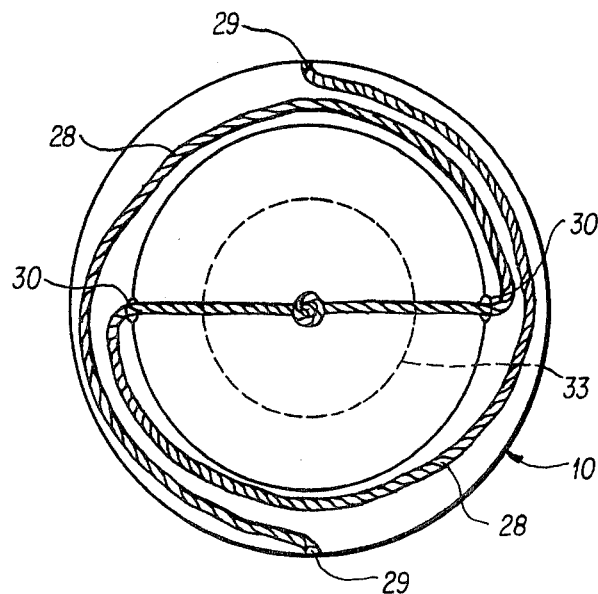
FIG. 4 is a top view, enlarged, of the flowered open end of the tampon.

FIG. 1 illustrates the exterior view of a tampon 10 as it appears in an insertion cylinder 12 and having an insertion plunger 14. This external view is not significantly different in appearance than other conventional tampons available.

The shelf form of the tampon device of FIG. 1 is illustrated in vertical section in the FIG. 3. Absorbency is provided by a body 16 of superabsorbent material of conventional nature. Body 16 is preferably substantially tubular with an open central area 17. It is preferable to have a completely open area 32, although an elongated cylindrical member with a gradually decreased density of absorbent material to the center may be employed with the advantages of this invention.

In the shelf form of FIG. 3, a forward end 18 projects from the forward end of the insertion cylinder 12. The forward end 18 has an annular perimeter wall 20 operable between a funnel-open configuration as shown in FIGS. 5 and 6, and a pursed condition as shown in FIG. 3 wherein the annular wall 20 is drawn onto the central axis of the tubular body.

Figure 5:
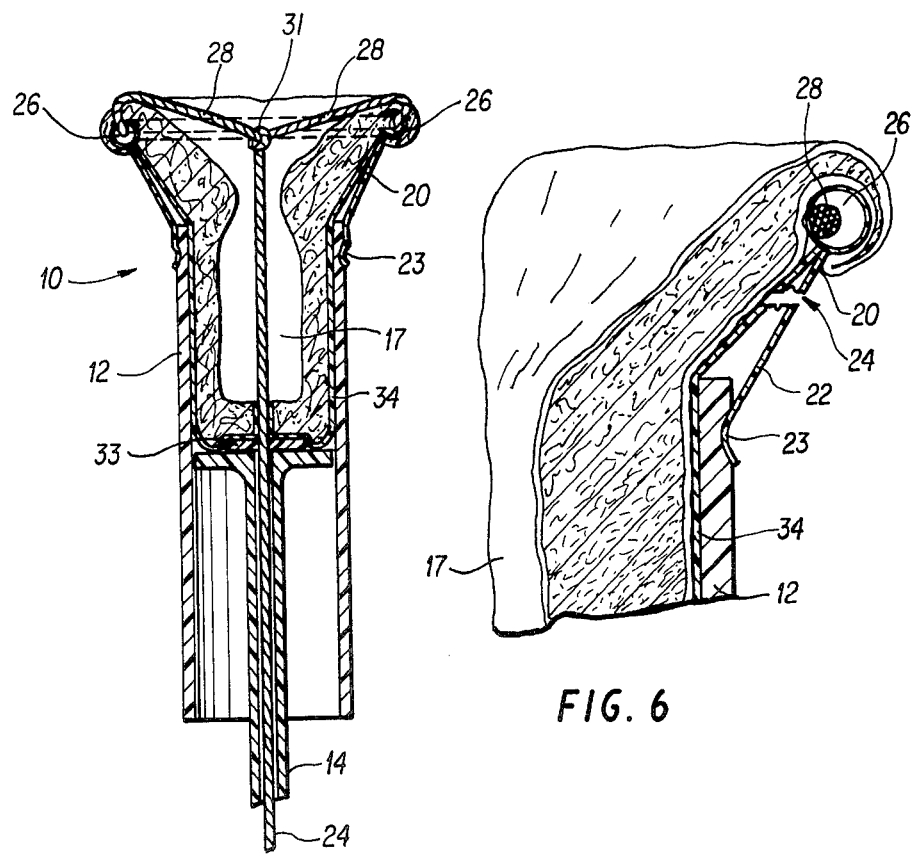
FIG. 5 illustrates a beginning step in the insertion wherein the membrane has caused the flowered opening.
Figure 6:
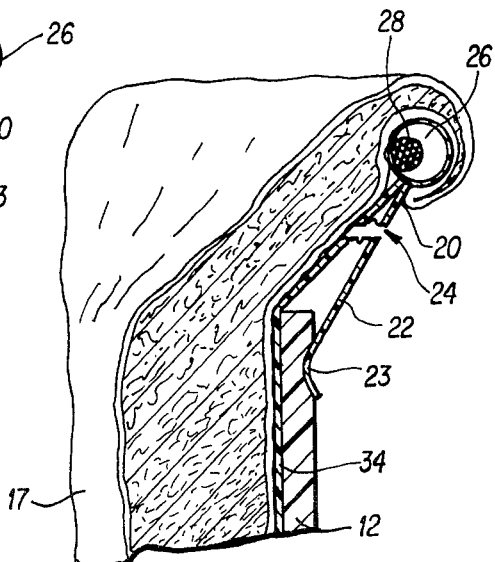
FIG. 6 illustrates the rupture of the restricting membrane as the tampon is further driven out of its carrier.

One of the principal objects of the invention is to flair the forward end 18 open to a funnel configuration, substantially as shown in FIGS. 5 and 6. This opening is sometimes referred to as a flowering open which refers to the opening from a bud to a mature flower condition.

To accomplish the flaring open of the forward end 18, the preferred embodiment employs an encasing membrane 22 which is secured to the area of the perimeter wall 20 and extends around to the forward end of the insertion cylinder 12 where it is secured in a fused area 23. A heat seal thermoplastic membrane is preferred, but a tie device of another material may otherwise be secured by adhesives. The membrane 22 is therefore very similar to a protective annulus over the end 18, but is employed for another purpose which supersedes any encapsulating function. That function is to cause the end 18 to flare.

Flaring of the end is achieved by moving the tampon out of the carrier in a forward direction by driving force of the plunger 14. As the tampon is thus ejected from its carrier, the membrane 22 will exert a restricting force to the perimeter wall 20 because of the limited length of the membrane. Thus, the perimeter wall 20 will begin to unfold and eventually reach the extreme condition shown in FIG. 5 wherein the membrane is stretched to its limit and the end 18 has fully flared to the open condition.

The membrane 22 is preferably formed with a tear strip 24 which is simply a weakened area or preferably a perforated area which will allow further drive of the tampon to exert a force on the membrane greater than the strength of the tear strip. Thus, severing of the membrane will take place as illustrated in the FIG. 6. Thereafter, the body of the tampon may be ejected from the insertion cylinder 12 and the forward end 18 of the tampon will be a funnel configuration that will move forward and essentially cap the cervix of the user and thereby enhance the directing of menstrual fluid into the tampon as opposed to seeping down around the exterior as in conventional practice.

Although a membrane 22 is the preferred form of the tie means restricting the end 18 to cause opening, a series of separate strips or strings has been found to be an acceptable alternative. These tie means, whichever form selected, is a means for spreading the forward end of the body to an open funnel configuration. The importance of the tie means is that it be of limited length and connect the insertion tube outer wall to the forward annular wall of the tampon body for limiting the outward movement of the body annular wall as the body is ejected from the insertion tube, whereby the annular wall is caused to flare to the open funnel configuration. It is also necessary to then have a means for severance of the tie means upon full opening of the forward end to the funnel configuration. This is done by preferably perforating a line around a membrane but does have alternative possibilities in weakened lines and tie devices.

After the tampon has been saturated, and the central area 17 filled with as much fluid as practical, a separate means is provided for drawing the forward end perimeter of the body in an inward and downward direction toward the center of the body, whereby the body forward end is closed to entrap menstrual fluid within the interior of the absorbent body.

The separate means for drawing the forward end inwardly is a drawstring in this preferred embodiment. The area of the perimeter wall 20 is preferably hemmed to form a channel 26 but could be separate belt loops or similar devices for forming a pursing action when a drawstring 28 is placed in the channel and drawn to shorten the string within the channel.

In FIG. 2, the drawstring is shown as it appears in the original package and after having been activated to draw the end closed. FIG. 4 illustrates the open funnel configuration. Both FIGS. 2 and 4 are somewhat schematic in that the hemmed channel is cut away to reveal the position of the drawstring 28 which would be obscured by showing the string encased within the confines of the channel.

Openings 30 on opposite sides of the perimeter wall 20 admit the drawstring into separate channel areas and the string is attached at opposite sides of the perimeter wall at points 29.

The drawstring is knotted by a knot 31 to cooperate with a support disk 33 at the base end of the cylinder 12 as illustrated best in FIG. 3. When the knot 31 is engaged in the central opening of disk 31, it can no longer be activated to draw the string beyond that limit, and thereafter will exert a uniform pull on the entire tampon. Thus, after the tampon is inserted and the insertion cylinder and plunger removed, the string 28 will serve as a combined closure means and withdrawal means to first pull the drawstring and purse the forward end of the tampon and thereafter, when the knot 31 strikes the support disk 33, the tampon will be removed from the vagina of the user.

This closing action is important in that any fluid absorbed to overcapacity in the funnel forward portion of the tampon is caused to flow downwardly and into the center area of the tampon rather than to flow out of the tampon into the vaginal channel.

In order to assure the capturing of the menstrual fluid and simultaneously prevent the overdrying and absorption of natural mucosa from the vagina channel, a moisture barrier 34 encapsulates the exterior of the tampon body from the area of the perimeter wall 20 to the bottom end of the tampon. Thus, as the pursing closing action takes place, the moisture barrier wall will cause the menstrual fluid to move downwardly into the central area of the tampon and prevent the loss of the fluid into the vaginal tract. Also, prior to that function, that barrier wall forms an exceedingly necessary and novel function in this improved tampon not heretofore available.

There has been much publicity about Toxic Shock Syndrome caused possibly by overabsorbency and subsequent ulceration caused by modern super absorbent materials used in tampons. In a publication *Annals of Internal Medicine*, a report in a conference held Nov. 20-22, 1982, sponsored by the Institute of Medicine and National Academy of Sciences, Volume 96, June 1982, reported on the pathological findings in twelve fatal cases of Toxic Shock Syndrome. That report said that there are notable pathological changes occuring in the vagina, cervix, lungs, liver, and kidney. And the report goes on to state that of these, the most striking pathological changes were noted in the vaginal, cervical mucosa. Extensive desquamation of the ulceration were seen in six of six patients where adequate vaginal/cervical sections were available.

The report is in detail and vital to the understanding of the overabsorbent relationship to the Toxic Shock Syndrome and concludes by stating that the findings of the study—normal endometrium without evidence of bacterial invasion associated with severely ulcerated cervical/vaginal mucosa showing evidence of superficial gram-positive bacterial invasion—suggests that access to the systemic circulation may be gained through cervical/vaginal blood or lymph vessels exposed by desquamation or ulceration. They state in this report that the vaginal tampon may be important in these processes. Excessive absorption of blood and of protective secretions may lead to mucosal drying and increased susceptibility so to superficial abrasion with both tampon insertion and withdrawal.

Although the report is very carefully worded not to directly attribute Toxic Shock Syndrome to tampon use and/or over absorption, it has been found that the barrier wall 34, provided for the containment of fluid, has performed the extremely important second function of prevention of vaginal wall drying. This structure will thereby fully eliminate any superabsorbency contribution to vaginal problems.

What is claimed is:

1. A tampon, comprising:
    an elongated body of absorbent material encapsulated in a moisture barrier;
    said body having a forward end terminating in a parameter wall;
    means for spreading the forward end perimeter wall of said body to an open funnel configuration;
    separate means for drawing the forward end perimeter wall of said body in an inward direction toward the center of the body, whereby the body forward end is opened upon insertion into the vagina of a menstruating female user such that the forwad end of the body in the open position essentially caps the cervix of such user and then is drawn closed to entrap menstrual fluid within the absorbent body.

2. A tampon device for the efficient entrapment of menstrual fluid, comprising:
    an elongated body of fluid absorbent material;
    said elongated body having a forward end and characterized by a central area which collects and holds menstrual fluid;
    an insertion tube, the elongated body housed in the tube;
    a plunger means for driving the elongated body in a forward directon from the insertion tube;
    the forward end of said elongated body having an annular wall operable between an open funnel configuration and a closed pursed condition wherein said annular wall is drawn inwardly and downwardly towards the central axis of the elongated body;
    a tie means of limited length connecting the insertion tube outer wall to the elongated body annular wall for limiting the outward movement of said elongated body annular wall as the body is ejected from said insertion tube, whereby the annular wall is caused to flair to the open funnel configuration;
    means for severance of the tie means upon full opening of said forward end to the funnel configuration; and
    draw means for the first reversing said flared annular wall of said tubular body to a closed, pursed configuration and then exerting a drive force for expulsion of said elongated body applied through the central cavity of said elongated body.

3. A tampon device for the efficient entrapment of fluid during menses, comprising:
    an insertion cylinder;
    a body of absorbent material residing within said insertion cylinder;
    an insertion plunger for ejecting said body from said insertion cylinder;
    said body having a forward end and a base end, the forward end of said body being closed in a drawn, pursed configuration during residency within said insertion cylinder, and the base end of said body being a closed configuration to retard fluid loss from the body interior;
    a fragile tethering means for securing the forward portion of said body to said insertion cylinder, the tethering means being of a length less than the forward movement of the body during ejection from the insertion cylinder whereby the pursed forward end is caused to flower out to an open funnel configuration, the tethering means thereafter rupturing to separate the body from the insertion cylinder; and
    a draw string pursing means attached to the forward end of the body and passing through a central channel within the body and out through the base end, whereby withdrawal force applied to said draw string is transmitted to the forward open funnel-configured end causing said forward end to again purse and continuation of withdrawal force on the draw string then causing the body to eject from the user.

4. A tampon as described in claim 1, the means for spreading the forward end of the elongated body into an open funnel configuration comprising:
   an insertion tube;
   an elongated body residing within said insertion tube; and
   a tie means membrane encasing the forward end and attached to the tube, the tie means membrane being of restricted length to thereby cause the forward end of the elongated body to roll outwardly to an open funnel configuration as the elongated body is ejected forwardly from the insertion tube and such tie means membrane having a break-away area for separation of the elongated body from the insertion tube.

5. A tampon device as described in claim 2, the draw means being a pursing string hemmed into a channel encompassing the forward end of the elongated body, the string bridging the open funnel configuration to limit the extent of funnel opening induced by the tie means.

6. A tampon device as described in claim 5, a draw string attached to the center of the pursing string and passing through the central cavity of the elongated body and out the bottom thereof, for causing the pursing of the forward end of said elongated body and to aid in withdrawal of such device from user.

7. As tampon device as described in claim 5, the elongated body having a moisture-barrier wall surrounding the outer wall of said elongated body.

8. A tampon device for the efficient entrapment of menstrual fluid without materially absorbing and drying of cervical-vaginal mucosa, comprising:
   a substantially tubular body of superabsorbent fiber, the tubular body having a forward end and a base end;
   the base end being substantially closed to retard fluid loss from the tubular body interior;
   the forward end having a draw string means for causing the tubular body to purse inwardly and downwardly when activated by the user;
   the forward end also having means for causing the tubular structure to flair to an open funnel formation as the tampon is inserted into the vagina, whereby the open flared end will cap the cervice of the user; and
   a barrier wall of fluid resistant material encapsulating the exterior wall of the body to prevent absorbancy from the vaginal wall.

* * * * *